(12) United States Patent
Fujii

(10) Patent No.: US 9,560,759 B2
(45) Date of Patent: Jan. 31, 2017

(54) POWER SUPPLY MODULE, PACKAGE FOR THE POWER SUPPLY MODULE, METHOD OF MANUFACTURING THE POWER SUPPLY MODULE AND WIRELESS SENSOR MODULE

(71) Applicant: SHINKO ELECTRIC INDUSTRIES CO., LTD., Nagano-shi, Nagano (JP)

(72) Inventor: Tomoharu Fujii, Nagano (JP)

(73) Assignee: SHINKO ELECTRIC INDUSTRIES CO., LTD., Nagano-Shi (JP)

( * ) Notice: Subject to any disclaimer, the term of this patent is extended or adjusted under 35 U.S.C. 154(b) by 0 days.

(21) Appl. No.: 14/876,116

(22) Filed: Oct. 6, 2015

(65) Prior Publication Data

US 2016/0105982 A1    Apr. 14, 2016

(30) Foreign Application Priority Data

Oct. 9, 2014  (JP) ................ 2014-208169

(51) Int. Cl.
| | |
|---|---|
| H05K 7/00 | (2006.01) |
| H05K 1/11 | (2006.01) |
| H01L 23/34 | (2006.01) |
| H05K 1/14 | (2006.01) |
| H05K 3/46 | (2006.01) |
| H05K 1/18 | (2006.01) |

(52) U.S. Cl.
CPC ............ *H05K 1/115* (2013.01); *H01L 23/34* (2013.01); *H05K 1/144* (2013.01); *H05K 3/4608* (2013.01); *H05K 3/4697* (2013.01); *H01L 2924/0002* (2013.01); *H05K 1/181* (2013.01); *H05K 1/183* (2013.01); *H05K 2201/10037* (2013.01)

(58) Field of Classification Search
CPC ..... H05K 1/144; H01F 21/02; H01L 23/5389; A61B 5/0205; A61B 5/0245; A61B 5/11
USPC ......................................................... 361/746
See application file for complete search history.

(56) References Cited

U.S. PATENT DOCUMENTS

| | | | | |
|---|---|---|---|---|
| 7,948,758 B2* | 5/2011 | Buhler | ................ | H01L 23/3735 29/837 |
| 2006/0043568 A1* | 3/2006 | Abe | .................... | H01L 21/4857 257/698 |
| 2009/0134459 A1* | 5/2009 | Goto | .................. | B81C 1/00246 257/347 |
| 2012/0318337 A1* | 12/2012 | Watanabe | ............. | H01L 31/075 136/255 |

(Continued)

FOREIGN PATENT DOCUMENTS

JP     2013-188422     9/2013

*Primary Examiner* — Hung S Bui
(74) *Attorney, Agent, or Firm* — Rankin, Hill & Clark LLP

(57) ABSTRACT

A package includes a metal core substrate, a first insulation layer formed along a periphery of a first surface of the metal core substrate, the first surface of the metal core substrate being exposed at an inner side of the first insulation layer, a second insulation layer formed along at least a periphery of a second surface of the metal core substrate, a first through-electrode penetrating the second insulation layer at a first part of the periphery of the metal core substrate, and a second through-electrode penetrating the first insulation layer, the metal core substrate and the second insulation layer at a second part of the periphery of the metal core substrate, the second through-electrode being electrically insulated from the metal core substrate via an insulation member.

10 Claims, 9 Drawing Sheets

(56) References Cited

U.S. PATENT DOCUMENTS

2015/0123284 A1* 5/2015 Jo ................... H01L 23/5384
257/774

* cited by examiner

POWER SUPPLY MODULE, PACKAGE FOR THE POWER SUPPLY MODULE, METHOD OF MANUFACTURING THE POWER SUPPLY MODULE AND WIRELESS SENSOR MODULE

CROSS-REFERENCE TO RELATED APPLICATION

The present application claims priority from Japanese Patent Application No. 2014-208169 filed on Oct. 9, 2014, the entire content of which is incorporated herein by reference.

BACKGROUND

Technical Field

The present disclosure relates to a power supply module including a battery and a circuit board having a voltage conversion circuit configured to convert a voltage of the battery into a predetermined voltage, a package for the power supply module and a method of manufacturing the power supply module. Further, the present disclosure relates to a wireless sensor module in which an electronic device having a wireless sensor function is stacked on the power supply module.

Related Art

A system attached to a body of human or animal and configured to remotely monitor the acquired information has been developed. More specifically, the system is configured to acquire biological information and exercise information, to wirelessly transmit the acquired information and to remotely monitor the information.

Patent Document 1 discloses a measurement device (wireless sensor) having a function of acquiring the information and wirelessly transmitting the same. In the measurement device disclosed in Patent Document 1, a sensor configured to acquire the biological information and the exercise information, a microcomputer configured to arithmetically process the acquired information, a transmission circuit configured to transmit the processed information, an antenna, and a holder configured to accommodate therein a battery for feeding power to these components are mounted on a circuit board and modularized.

[Patent Document 1] Japanese Patent Application Publication No. 2013-188422A

In the wireless sensor module disclosed in Patent Document 1, since the holder configured to accommodate therein the battery is mounted on the circuit board, a size of the wireless sensor module is restricted by a size of the holder. For this reason, it is difficult to make the entire wireless sensor module small and thin.

In the meantime, it is necessary to provide the wireless sensor module with the battery configured to feed the power to the components such as the sensor and the microcomputer, and the voltage conversion circuit for lowering a voltage of the battery to an operating voltage of the microcomputer and the like.

Therefore, if a power supply module is configured by the battery and the voltage conversion circuit and the power supply module can be made to be small and thin, it is possible to implement a small and thin wireless sensor module by stacking an electronic device having a wireless sensor function on the power supply module.

SUMMARY

Exemplary embodiments of the invention provide a small and thin power supply module, a package for the power supply module, a method of manufacturing the power supply module, and a wireless sensor module including the power supply module.

A package according to an exemplary embodiment of the invention comprises:

a metal core substrate;

a first insulation layer formed along a periphery of a first surface of the metal core substrate, the first surface of the metal core substrate being exposed at an inner side of the first insulation layer;

a second insulation layer formed along at least a periphery of a second surface of the metal core substrate;

a first through-electrode penetrating the second insulation layer at a first part of the periphery of the metal core substrate; and a second through-electrode penetrating the first insulation layer, the metal core substrate and the second insulation layer at a second part of the periphery of the metal core substrate, the second through-electrode being electrically insulated from the metal core substrate via an insulation member.

A power supply module according to an exemplary embodiment of the invention comprises:

the package;

a battery mounted over a metal core substrate; and a circuit board mounted on the metal core substrate and having a voltage conversion circuit configured to convert a voltage of the battery into a predetermined voltage, wherein the battery is mounted on the first surface of the metal core substrate at a state where one electrode terminal of the battery is contacted to the first surface, wherein the circuit board having the voltage conversion circuit is mounted at the second surface-side of the metal core substrate, wherein the one electrode terminal of the battery is connected to the first through-electrode via the metal core substrate, wherein the other electrode terminal of the battery is connected to the second through-electrode exposed to a surface of the first insulation layer via a connection member, and wherein potentials of both the electrode terminals of the battery are respectively supplied to the circuit board via the first through-electrode and the second through-electrode exposed to a surface of the second insulation layer.

According to the present invention, it is possible to provide the small and thin power supply module, the package for the power supply module, the method of manufacturing the power supply module, and the wireless sensor module including the power supply module.

DETAILED DESCRIPTION

Figure 1A:
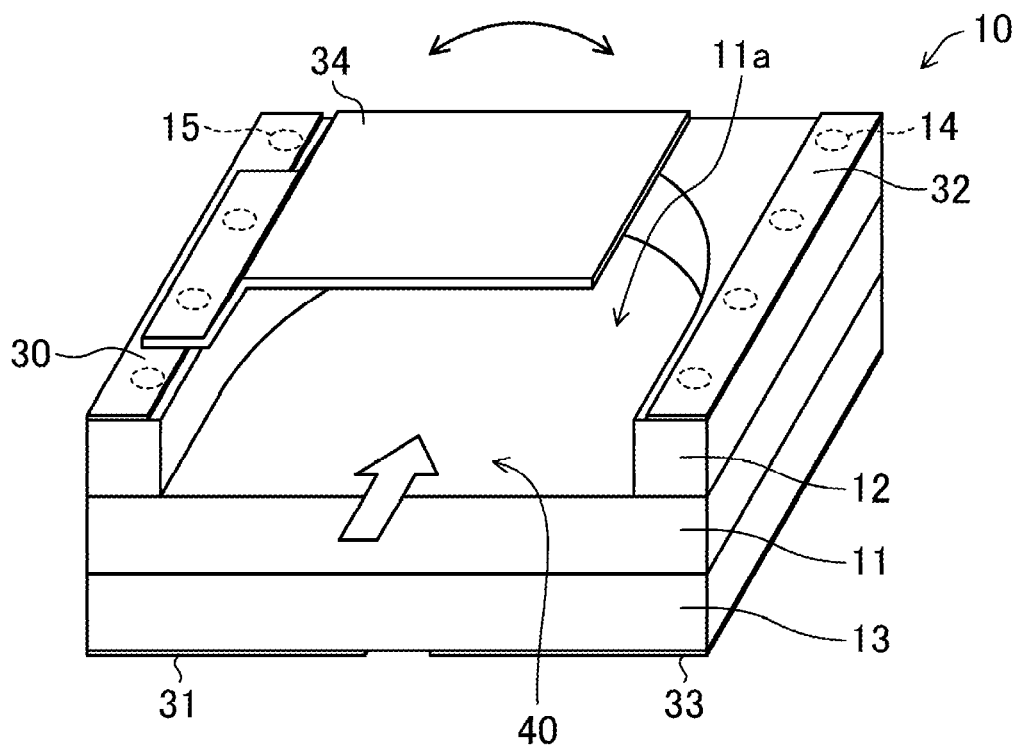
FIGS. 1A and 1B are perspective views illustrating a part of a configuration of a power supply module according to an exemplary embodiment of the present invention.

Before describing exemplary embodiments of the present invention, the development to the present invention is described.

The inventor considered making a small and thin power supply module by using a full solid secondary battery, and performed a variety of studies.

The inventor found that, when a wireless sensor module is configured by stacking a package (electronic device) having a wireless sensor function on a power supply module, following problems occurs. That is, since a transmission circuit, which is one of the components configuring the wireless sensor module and is configured to wirelessly transmit the information acquired through a sensor, has high power of consumption and a battery embedded in a silicon substrate has a small capacity, it is difficult to prolong the operating time of the wireless sensor module.

Therefore, the inventor focused on a coin type battery having a larger capacity. A thickness of the standardized coin type battery is thick such as 3 mm or greater. However, the inventor found that even when the thickness of the coin type battery is made to be thin such as 2 mm or smaller, the coin type battery has a sufficient capacity, as the battery for feeding power of the wireless sensor module.

However, even though the thickness of the battery is made to be thin, when the battery is mounted on the circuit board with the battery attached to the holder, a whole size of the power supply module is restricted by a size of the holder, so that it is not possible to accomplish the effect, which is to be obtained as the battery is made to be small.

Therefore, the inventor focused on a metal core substrate of which both surfaces are formed with insulation layers. That is, the inventor found that, when a part of the insulation layer formed on one surface is removed to expose the core substrate and the battery is directly mounted thereto, the core substrate can be used as one electrode of the battery. Thereby, when a via is formed in the insulation layer formed on the other surface, it is possible to take out a potential of one electrode of the battery from a surface of the insulation layer via the core substrate. Also, since the area in which the insulation layer has been removed can be configured as a cavity for accommodating the battery, it is possible to implement a power supply module that is not restricted by the thickness of the battery. Further, since the battery is directly contacted to the core substrate, it is possible to effectively radiate the heat generated from the battery.

That is, the battery is directly mounted on the exposed metal core substrate, so that the holder is not required. Also, a circuit board having a voltage conversion circuit is stacked on the metal core substrate, so that it is possible to make the power supply module small and thin.

Hereinafter, exemplary embodiments of the present invention will be described in detail with reference to the drawings. In the meantime, the present invention is not limited to the exemplary embodiments. Also, the exemplary embodiments can be appropriately changed without departing from the scope in which the effects of the present invention are accomplished.

Figure 1B:
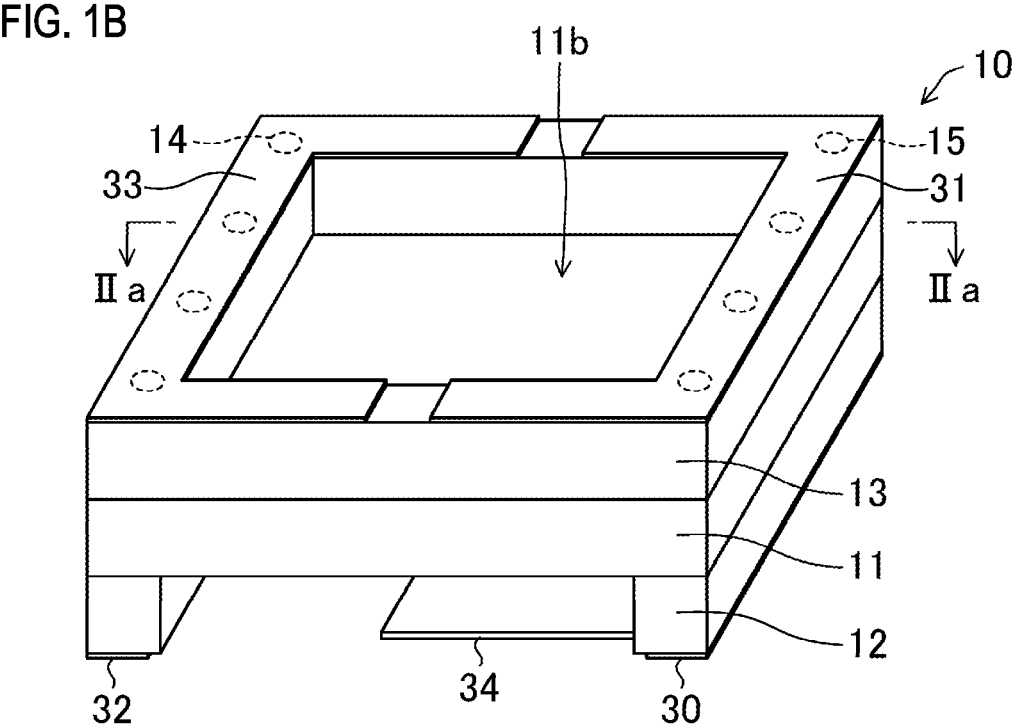

FIGS. 1A and 1B illustrate a part of a configuration of a power supply module according to an exemplary embodiment of the present invention, in which FIG. 1A is a perspective view and FIG. 1B is a perspective view illustrating a reversed state in an arrow direction from a state of FIG. 1A. Also, FIG. 2A is a sectional view taken along a line IIa-IIa of FIG. 1B, and FIG. 2B is a bottom view.

Figure 2A:
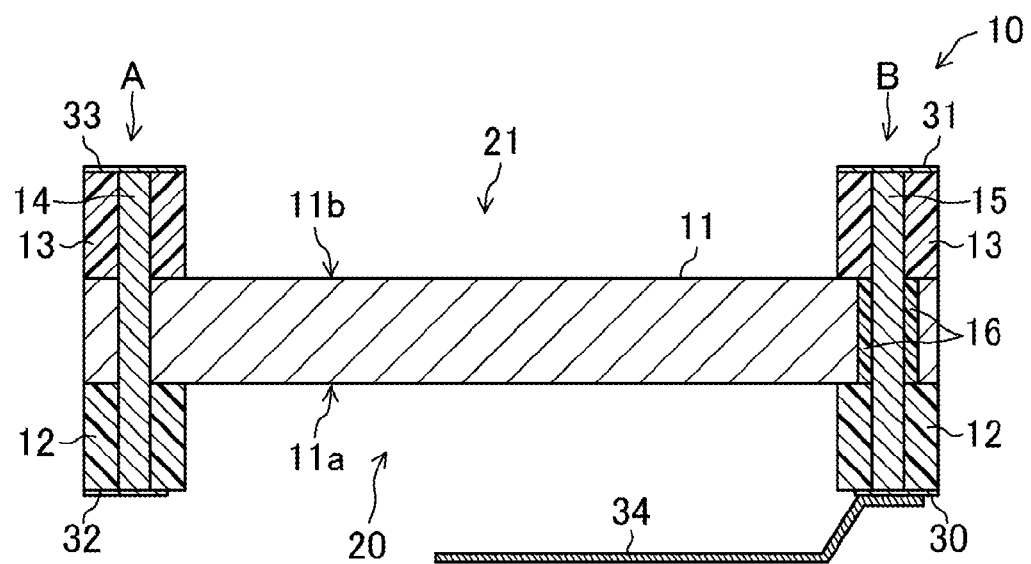
FIG. 2A is a sectional view taken along a line IIa-IIa of FIG. 1B.

As shown in FIGS. 1A and 2A, a first surface 11a of a metal core substrate 11 is formed with a first insulation layer 12 along a periphery of the metal core substrate 11, and the first surface 11a of the metal core substrate 11 is exposed at an inner side of the first insulation layer 12. Thereby, a first cavity 20 defined by the first surface 11a at which the metal core substrate 11 is exposed and side surfaces of the first insulation layer 12 is formed at the inner side of the first insulation layer 12.

Figure 2B:
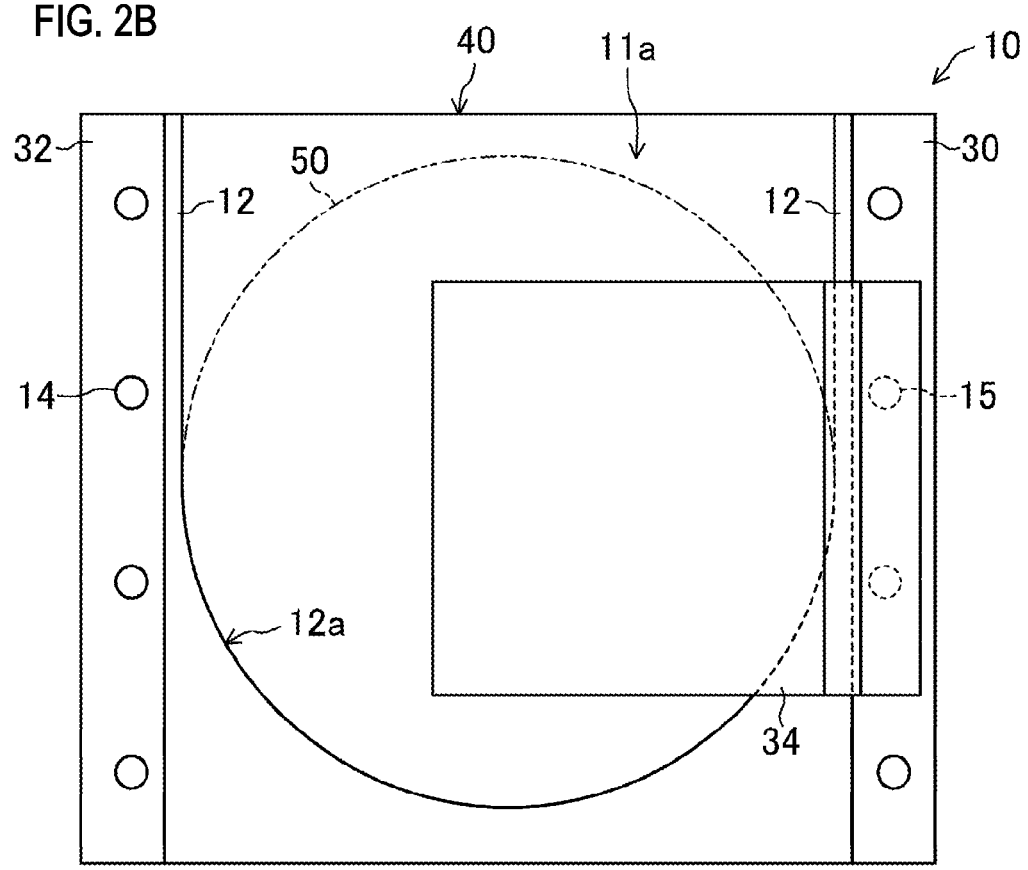
FIG. 2B is a bottom view.

Here, as shown in FIGS. 1A and 2B, the first insulation layer 12 is formed along three sides of the metal core substrate 11, and one side at which the first insulation layer 12 is not formed serves as an opening 40 for attaching and detaching a coin type battery (hereinafter, simply referred to as 'battery') to and from the first cavity 20.

Here, as shown in FIGS. 1A and 2B, a second surface 11b of the metal core substrate 11 is formed with a second insulation layer 13 along a periphery of the metal core substrate 11, and the second surface 11b of the metal core substrate 11 is exposed at an inner side of the second insulation layer 13. Thereby, a second cavity 21 defined by the second surface 11b at which the metal core substrate 11 is exposed and side surfaces of the second insulation layer 13 is formed at the inner side of the second insulation layer 13.

As shown in FIG. 2A, a first part A at the periphery of the metal core substrate 11 is formed with first through-electrodes 14 penetrating the first insulation layer 12, the metal core substrate 11 and the second insulation layer 13. Also, a second part B at the periphery of the metal core substrate 11 is formed with second through-electrodes 15 penetrating the first insulation layer 12, the metal core substrate 11 and the second insulation layer 13. Here, the second through-electrode 15 penetrating the metal core substrate 11 is electrically insulated from the metal core substrate 11 via an insulation member 16 formed around the second through-electrode 15.

Also, plate electrodes 30, 31, 32, 33 are respectively formed on the first through-electrodes 14 and second through-electrodes 15 exposed to surfaces of the first insulation layer 12 and second insulation layer 13. Further, the second through-electrodes 15 exposed to the surface of the first insulation layer 12 are provided with a connection member 34 that is to be connected to one electrode terminal of a battery.

Also, as shown in FIG. 2B, at least a part of the first insulation layer 12 has an arc-shaped side surface 12a configured to contact an outer periphery (a side surface) of a battery 50.

Figure 3:
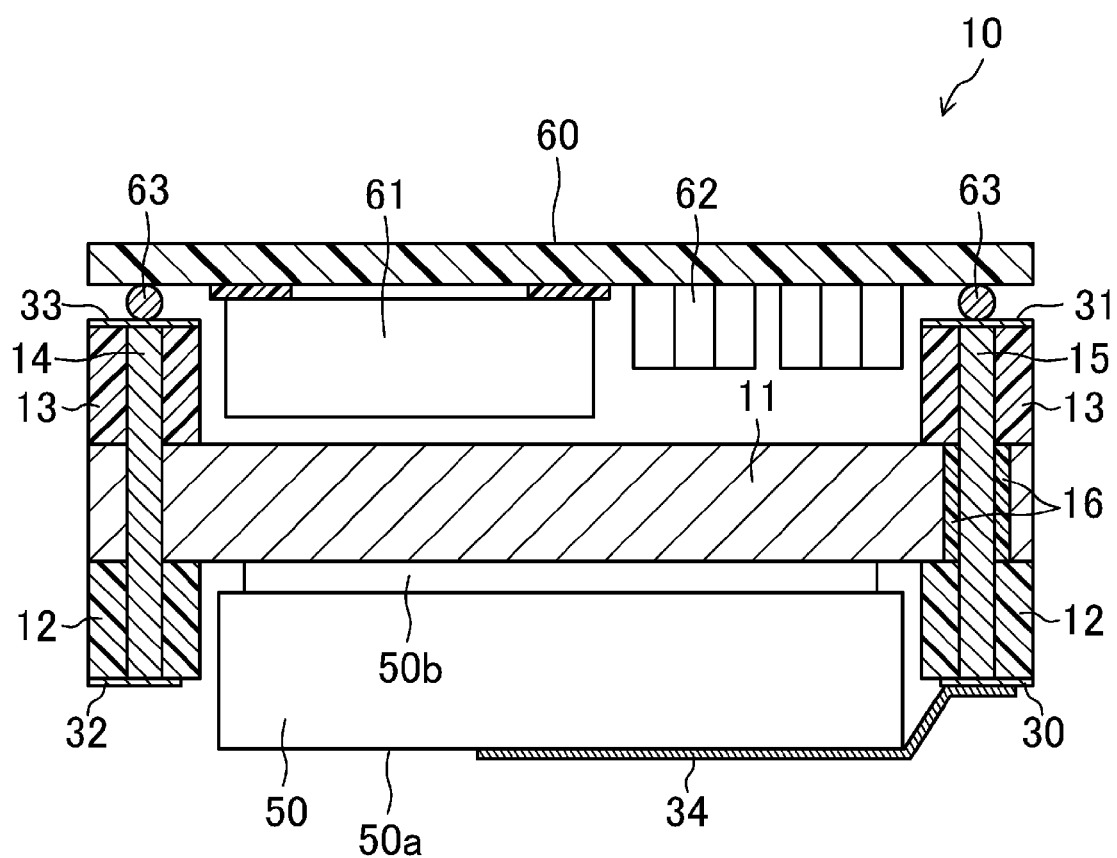
FIG. 3 is a sectional view illustrating the configuration of the power supply module according to the exemplary embodiment of the present invention.

FIG. 3 is a sectional view illustrating a configuration of the power supply module 10 according to the exemplary embodiment of the present invention.

As shown in FIG. 3, the battery 50 is mounted on the first surface 11a of the metal core substrate 11 at a state where a negative terminal (one electrode terminal) 50b of the battery is contacted to the first surface 11a. Thereby, the metal core substrate 11 becomes a negative pole of the battery 50. Also, a positive terminal (the other electrode terminal) 50a of the battery 50 is connected to the second through-electrodes 15 exposed to the surface of the first insulation layer 12 via the connection member 34. In the meantime, the battery 50 is accommodated in the first cavity 20 formed at the inner side of the first insulation layer 12.

In the meantime, a circuit board 60 having voltage conversion circuits 61, 62 mounted thereon is flip-chip mounted at the second surface 11b-side of the metal core substrate 11. Here, the circuit board 60 is mounted so that a surface thereof on which the voltage conversion circuits 61, 62 are mounted faces towards the metal core substrate 11. Thereby, the voltage conversion circuits 61, 62 are accommodated in the second cavity 21 formed at the inner side of the second insulation layer 13.

By the above configuration, the negative terminal 50b of the battery 50 is connected to the first through-electrodes 14 via the metal core substrate 11. Also, the positive terminal 50a of the battery 50 is connected to the second through-electrodes 15 via the connection member 34. Also, the first through-electrodes 14 and the second through-electrodes 15 exposed to the surface of the second insulation layer 13 are respectively connected to input terminals (not shown) of the voltage conversion circuits 61, 62 mounted on the circuit board 60 via bumps 63. That is, the potentials of the positive and negative terminals 50a, 50b of the battery 50 are respectively supplied to the circuit board 60 via the first through-electrodes 14 and the second through-electrodes 15 exposed to the surface of the second insulation layer 13. The voltage conversion circuits 61, 62 are configured to convert a voltage of the battery 50 input to the input terminals into a predetermined voltage, and to output the same from output terminals (not shown).

According to the power supply module 10 of this exemplary embodiment, the battery 50 is directly mounted on the metal core substrate 11, which is exposed by removing a part of the first insulation layer 12, so that it is possible to implement the small and thin power supply module without a holder. Also, the battery 50 is accommodated in the first cavity 20 formed at the inner side of the first insulation layer 12, so that it is possible to implement the thin power supply module, which is not restricted by a thickness of the battery 50. Further, since the battery 50 is directly contacted to the metal core substrate 11, it is possible to effectively radiate the heat generated from the battery 50 towards an outside.

Also, according to this exemplary embodiment, it is possible to supply the potentials of the positive and negative terminals 50a, 50b of the battery 50 to the circuit board 60 via the first through-electrodes 14 and the second through-electrodes 15 exposed to the surface of the second insulation layer 13. For this reason, it is possible to supply the potentials of the battery to the input terminals of the voltage conversion circuits by mounting the circuit board 60 on the second insulation layer 13 with the flip-chip connection without forming a useless wiring structure.

Also, as shown in FIG. 2B, the side surface 12a of at least a part of the first insulation layer 12 is formed to have an arc shape contacting the outer periphery of the battery 50, so that it is possible to keep the battery 50 accommodated in the first cavity 20.

Also, according to the exemplary embodiment, the voltage conversion circuits 61, 62 are accommodated in the second cavity 21 formed at the inner side of the second insulation layer 13, so that it is possible to implement the thinner power supply module.

Also, according to the exemplary embodiment, when the voltage conversion circuits 61, 62 are changed, it is possible to supply the output voltage corresponding to a variety of operating voltages. Also, when a package (electronic device) having a variety of functions is stacked on the power supply module of the exemplary embodiment, it is possible to implement a small and thin function module.

Also, as shown in FIG. 1A, the plate electrodes 30, 32 formed on the first insulation layer 12 are formed with being retreated from an inner edge portion of the first insulation layer 12, so that it is possible to prevent the short with the battery 50 accommodated in the first cavity 20.

In this exemplary embodiment, a material of the metal core substrate is not particularly limited. For example, a copper substrate may be used. Also, the materials of the first and second insulation layers are not particularly limited. For example, an epoxy-based material may be used. Also, the materials of the first and second through-electrodes 14, 15 are not particularly limited. For example, copper formed by the electrolytic plating may be used.

Also, in this exemplary embodiment, the structure of the battery 50 is not particularly limited in as much as the positive terminal 50a and the negative terminal 50b are opposite to face each other. Also, the type of the battery is not particularly limited. That is, a primary battery or a secondary battery may be used.

Also, the configuration shown in FIGS. 1A to 2B may be an exemplary embodiment of the package that is to be used for the power supply module 10.

That is, the package of the exemplary embodiment includes the metal core substrate 11, the first insulation layer 12 formed on the first surface 11a of the metal core substrate 11, and the second insulation layer 13 formed on the second surface 11b of the metal core substrate 11. The first insulation layer 12 is formed along the periphery of the metal core substrate 11, and the first surface 11a of the metal core substrate 11 is exposed at the inner side of the first insulation layer 12. Also, the second insulation layer 13 is formed along at least the periphery of the metal core substrate 11. The first part A at the periphery of the metal core substrate 11 is formed with the first through-electrodes 14 penetrating the first insulation layer 12, the metal core substrate 11 and the second insulation layer 13. Also, the second part B at the periphery of the metal core substrate 11 is formed with the second through-electrodes 15 penetrating the first insulation layer 12, the metal core substrate 11 and the second insulation layer 13, and the second through-electrode 15 penetrating the metal core substrate 11 is electrically insulated from the metal core substrate 11 via the insulation member 16.

According to the package of this exemplary embodiment, when the battery 50 is mounted on the first surface of the metal core substrate so that the negative terminal (one electrode terminals) 50b is contacted to the first surface 11a of the metal core substrate and the circuit board 60 having the voltage conversion circuits 61, 62 is mounted at the second surface 11b-side of the metal core substrate 11, the negative terminal 50b of the battery 50 is connected to the first through-electrodes 14 via the metal core substrate 11 and the positive terminal 50a of the battery 50 is connected to the second through-electrodes 15 exposed to the surface of the first insulation layer 12. Thereby, the potentials of both the electrode terminals 50a, 50b of the battery 50 are respectively supplied to the circuit board 60 via the first through-electrodes 14 and second through-electrodes 15 exposed to the surface of the second insulation layer 13.

Subsequently, a method of manufacturing the power supply module of the exemplary embodiment is described with reference to FIGS. 4A to 4D.

Figure 4A:
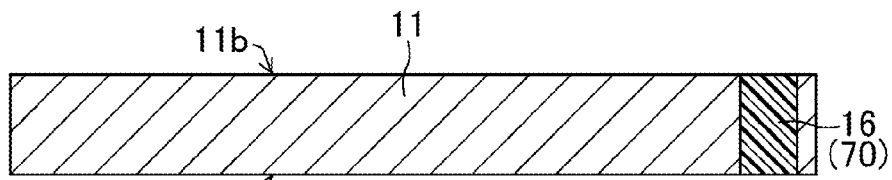
FIGS. 4A to 4D are sectional views illustrating a method of manufacturing the power supply module according to the exemplary embodiment of the present invention.

First, as shown in FIG. 4A, the metal core substrate 11 is formed with through-holes 70, and the insulation member 16 is embedded in the through-holes 70. As the metal core substrate 11, a copper substrate may be used, for example. As the insulation member 16, an epoxy-based resin may be used, for example.

Figure 4B:
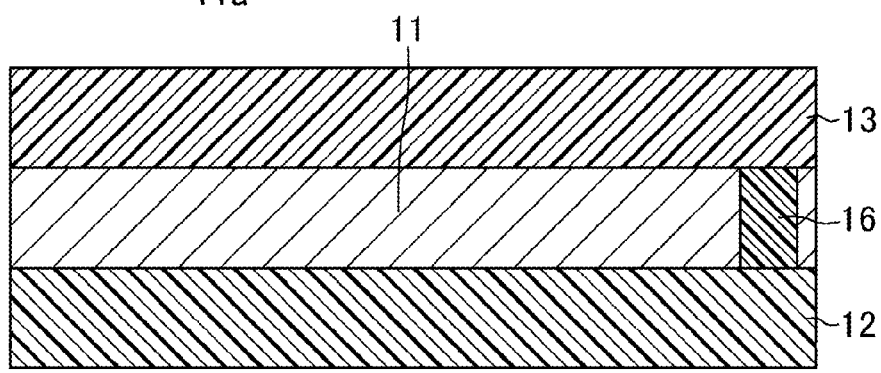

Then, as shown in FIG. 4B, the first insulation layer 12 and the second insulation layer 13 are formed on the first surface 11a and the second surface 11b of the metal core substrate 11, respectively. The first and second insulation layers 12, 13 may be formed by bonding epoxy-based resin sheets of a semi-cured state (B stage) to the surfaces of the metal core substrate 11 and then curing the same by heating/pressurization. In the meantime, the through-holes 70 may be filled with the first and second insulation layers 12, 13 by bonding the first insulation layer 12 and the second insulation layer 13 on the first surface 11a and the second surface 11b of the metal core substrate 11, respectively, and then pressurizing the same.

Figure 4C:
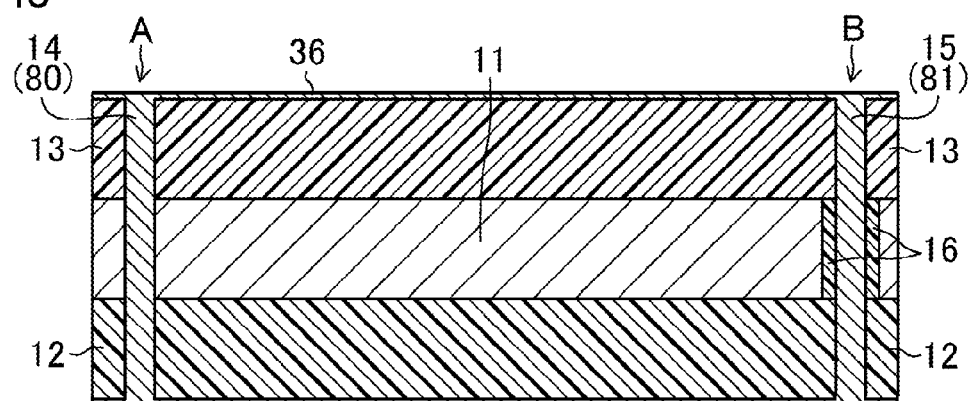

Then, as shown in FIG. 4C, the first part A at the periphery of the metal core substrate 11 is formed with through-holes 80 penetrating the first insulation layer 12, the metal core substrate 11 and the second insulation layer 13. Also, at the same time, the second part B at the periphery of the metal core substrate 11 is formed with through-holes 81 penetrating the first insulation layer 12, the insulation member 16 of the metal core substrate 11 and the second insulation layer 13. In the meantime, a diameter of the through-hole 81 is smaller than a diameter of the through-hole 70 formed in the metal core substrate 11. The through-holes 80, 81 may be formed by drilling or laser processing, for example. After that, the first through-electrodes 14, the second through-electrodes 15, and conductive layer 35, 36 are respectively formed in the through-holes 80, 81 and on the first and second insulation layers 12, 13. They may be formed using the copper electrolytic plating, for example.

Figure 4D:
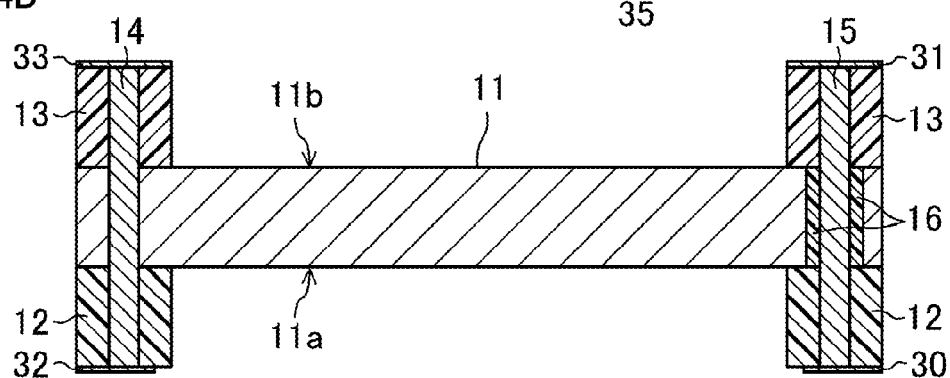

Then, as shown in FIG. 4D, the first insulation layer 12 and the conductive layer 35 are removed with being left at the periphery of the metal core substrate 11, so that the first surface 11a of the metal core substrate 11 is exposed. Also, likewise, the second insulation layer 13 and the conductive layer 36 are removed with being left at the periphery of the metal core substrate 11, so that the second surface 11b of the metal core substrate 11 is exposed. The removal of the first and second insulation layers 12, 13 and the conductive layer 35, 36 may be performed by router processing, for example.

Lastly, the positive terminal is contacted to the first surface 11a of the metal core substrate 11, so that the battery 50 is mounted. The battery 50 may be bonded to the metal core substrate 11 by using an adhesive material, for example. Also, the circuit board 60 having the voltage conversion circuits 61, 62 is mounted at the second surface 11b-side of the metal core substrate 11 by the flip-chip connection. Thereby, the power supply module 10 shown in FIG. 3 is completed.

Meanwhile, in the manufacturing method of the power supply module according to the exemplary embodiment, the processes shown in FIGS. 4A and 4B may be a process of preparing in advance the metal core substrate 11 of which the first surface 11a and the second surface 11b are formed with the first insulation layer 12 and the second insulation layer 13, respectively, and the insulation member 16 is embedded in a thickness direction at the periphery.

Figure 5A:
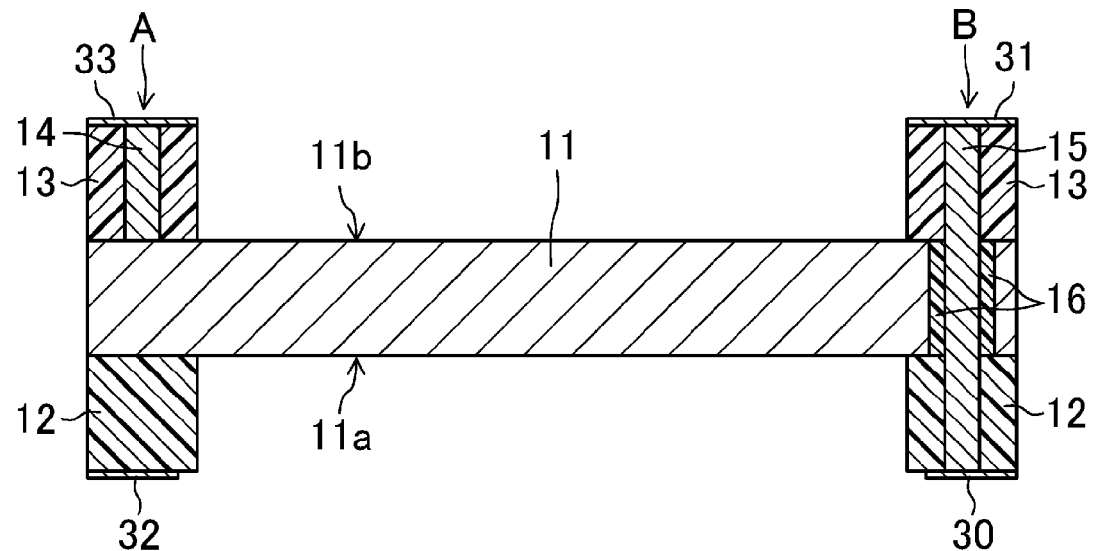
FIGS. 5A and 5B are sectional views illustrating modified embodiments of the power supply module.
Figure 5B:
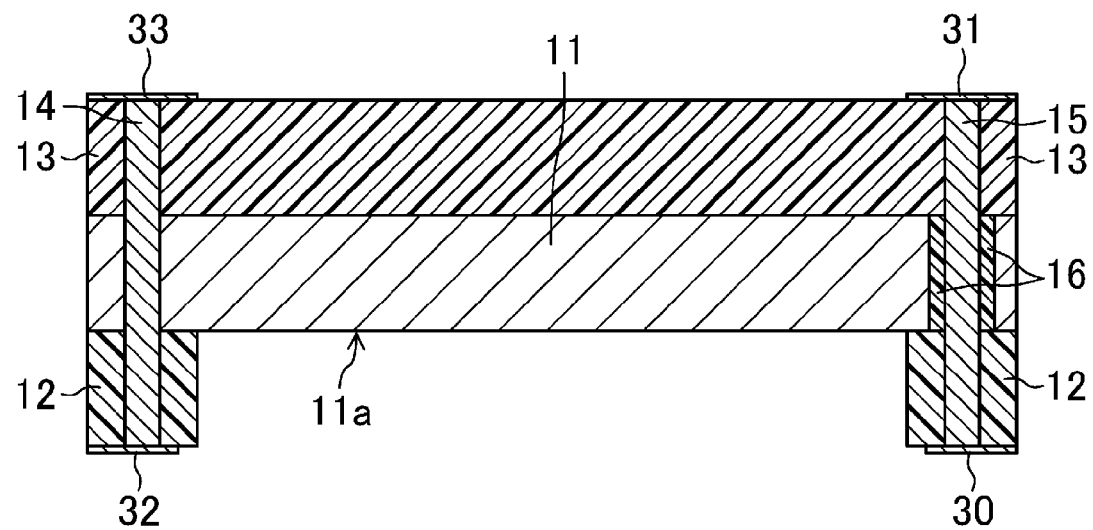

FIGS. 5A and 5B illustrate modified embodiments of the power supply module of the exemplary embodiment and correspond to FIG. 2A. Here, the connection member 34 is omitted.

According to the modified embodiment shown in FIG. 5A, the first part A at the periphery of the metal core substrate 11 is formed with the first through-electrodes 14 shown in FIG. 4A to penetrate the second insulation layer 13.

In this modified embodiment, the first through-electrodes 14 are connected to the second surface 11b of the metal core substrate 11. For this reason, when the battery 50 is mounted on the first surface 11a of the metal core substrate 11, the negative terminal 50b is connected to the first through-electrodes 14 via the metal core substrate 11. Thereby, the potential of the negative terminal 50b of the battery 50 can be supplied to the circuit board 60 via the first through-electrodes 14 exposed to the surface of the second insulation layer 13.

In a modified embodiment shown in FIG. 5B, instead of the configuration where the second surface 11b of the metal core substrate 11 is exposed at the inner side of the second insulation layer 13, like FIG. 2A, the second insulation layer 13 is formed over the entire surface of the second surface 11b of the metal core substrate 11. Thereby, since the metal core substrate 11 can be supported with the second insulation layer 13, it is possible to increase the strength of the metal core substrate 11.

Figure 6A:
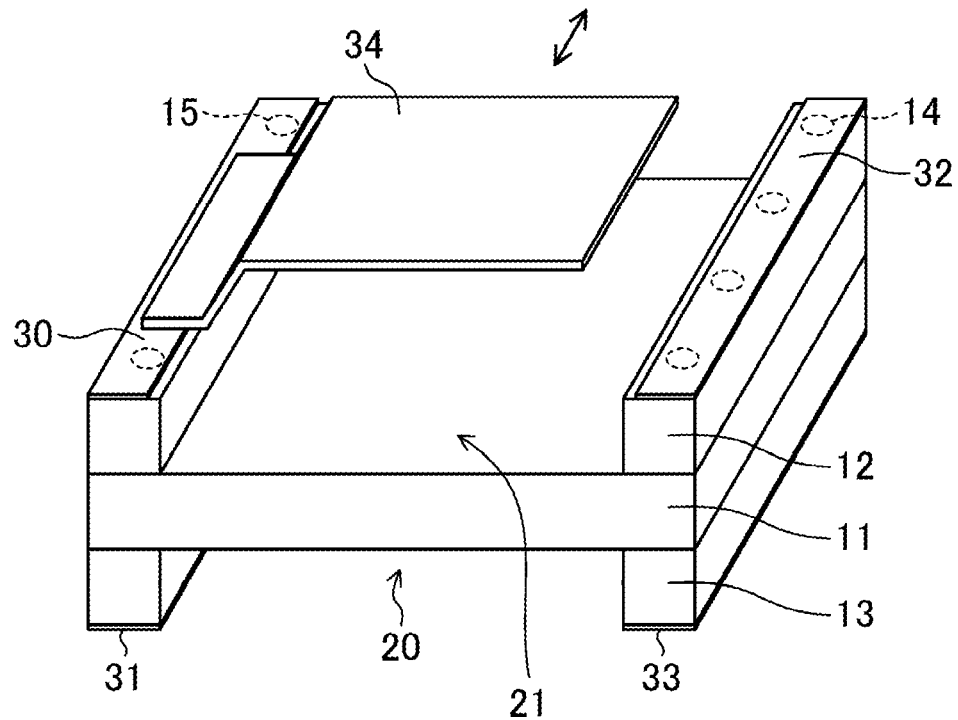
FIGS. 6A and 6B are perspective views illustrating other modified embodiments of the power supply module.
Figure 6B:
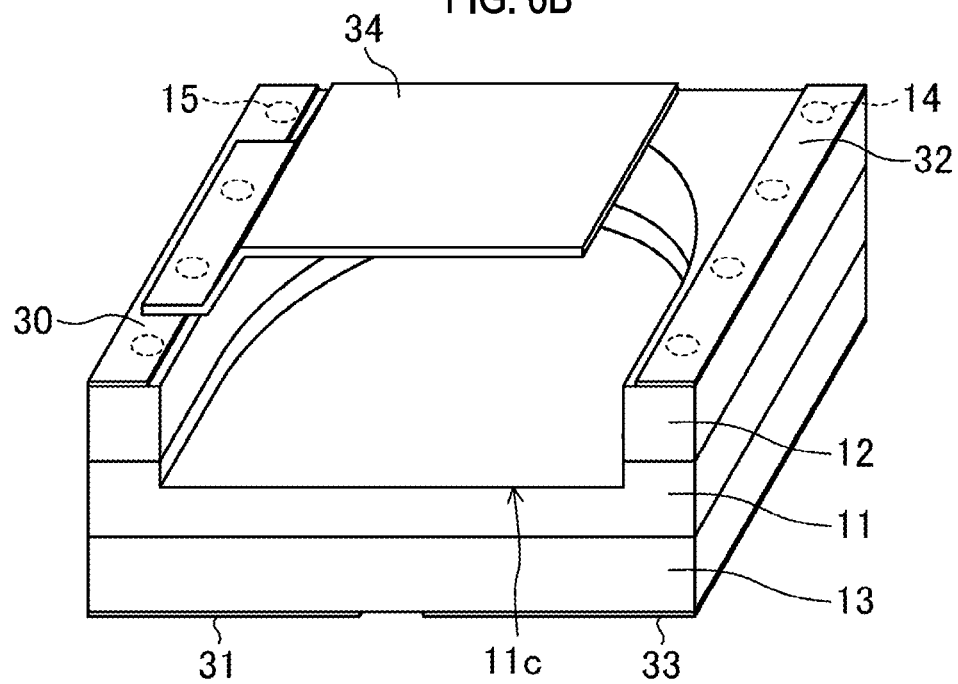

FIGS. 6A and 6B illustrate other modified embodiments of the power supply module of the exemplary embodiment, and correspond to FIG. 1A.

In the modified embodiment shown in FIG. 6A, the first and second insulation layers 12, 13 are formed along only two opposite sides of the metal core substrate 11. That is, the cavities 20, 21 formed on both surfaces of the metal core substrate 11 are opened in an arrow direction in FIG. 6A. Thereby, when resin-molding the power supply module 10 having the battery 50 and the circuit board 60 to the metal core substrate 11, it is possible to easily fill the cavities 20, 21 with the resin.

In the modified embodiment shown in FIG. 6B, the exposed first surface 11a of the metal core substrate 11 has a step portion 11c with respect to the first insulation layer 12. The step portion 11c may be formed in the process of FIG. 4D by additionally removing a part of the surface of the metal core substrate 11 when removing the first insulation layer 12 with being left at the periphery of the metal core substrate 11. Thereby, when the battery 50 is mounted on the first surface 11a of the metal core substrate 11, a side surface of the battery 50 is contacted to a side surface of the step portion 11c of the metal core substrate 11, so that it is possible to more securely hold the battery 50. In the meantime, the step portion 11c may further have an inclined surface deepening from the opening 40 towards an inner side thereof.

Figure 7:
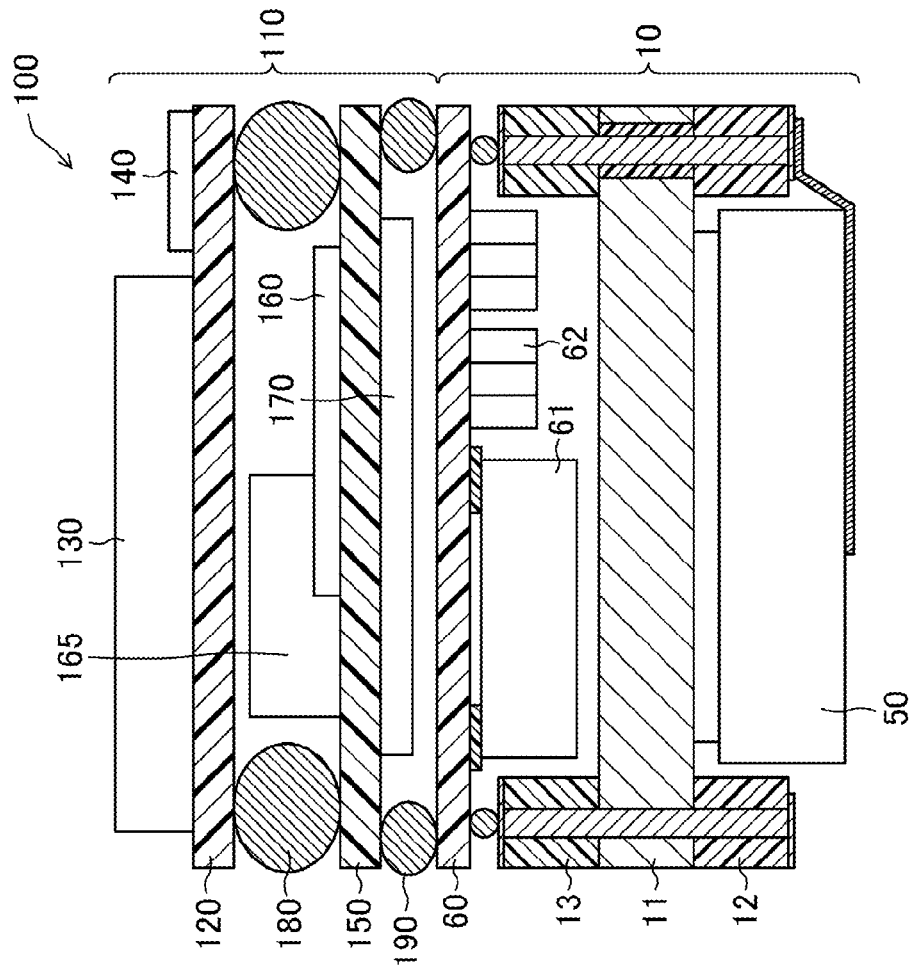
FIG. 7 is a sectional view illustrating a configuration of a wireless sensor module according to another exemplary embodiment of the present invention.

FIG. 7 is a sectional view illustrating a configuration of a wireless sensor module 100 according to another exemplary embodiment of the present invention.

As shown in FIG. 7, the wireless sensor module 100 of this exemplary embodiment forms a configuration where an electronic device 110 having a wireless sensor function is stacked on the power supply module 10 shown in FIG. 3. Here, the power supply module 10 has the same configuration as the above exemplary embodiment.

In this exemplary embodiment, the electronic device 110 has a sensor 130, an antenna 140 configured to transmit a detection signal detected at the sensor 130, and a circuit board 150 on which the sensor 130 and the antenna 140 are mounted. The sensor 130 is a device configured to detect the biological information such as pulsation, blood pressure and aspiration and the exercise information such as a motion of each part of a body. For example, a biological potential electrode sensor, an acceleration sensor and the like may be used. Also, the circuit board 150 is mounted with a microcomputer 160 configured to arithmetically process the information acquired at the sensor 130, a transmission circuit 165 configured to transmit the processed information and a memory 170 configured to store therein the processed information. The circuit boards 120, 150 are flip-chip mounted to the circuit board 60 via bumps 180, 190.

By the above configuration, according to the wireless sensor module 100 of this exemplary embodiment, the output voltages of the voltage conversion circuits 61, 62 of the power supply module 10 are supplied as driving voltages of the sensor 130 and the antenna 140. Thereby, the wireless sensor module 100 operates using the battery 50 mounted to the power supply module 10, as a driving power supply.

According to this exemplary embodiment, since the electronic device 110 having a wireless sensor function is stacked on the small and thin power supply module 10, so that the wireless sensor module 100 is configured, it is possible to implement the small and thin wireless sensor module 100. Also, since the battery 50 is directly contacted to the metal core substrate 11, it is possible to effectively radiate the heat generated from the battery 50 towards the outside. Therefore, even when the wireless sensor module 100 is attached to the body, for example, the body is not exposed to the high temperatures.

Figure 8:
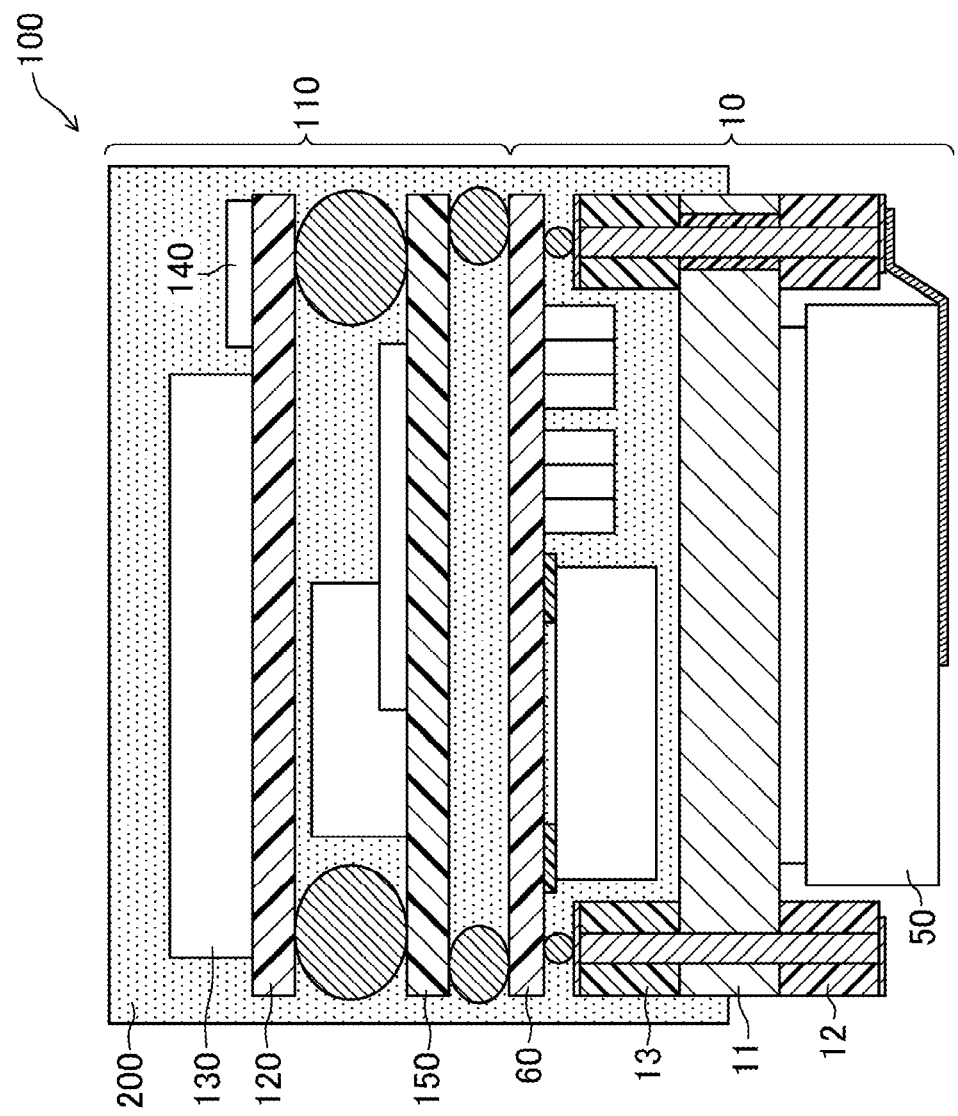
FIG. 8 is a sectional view illustrating a modified embodiment of the wireless sensor module.
Figure 9:
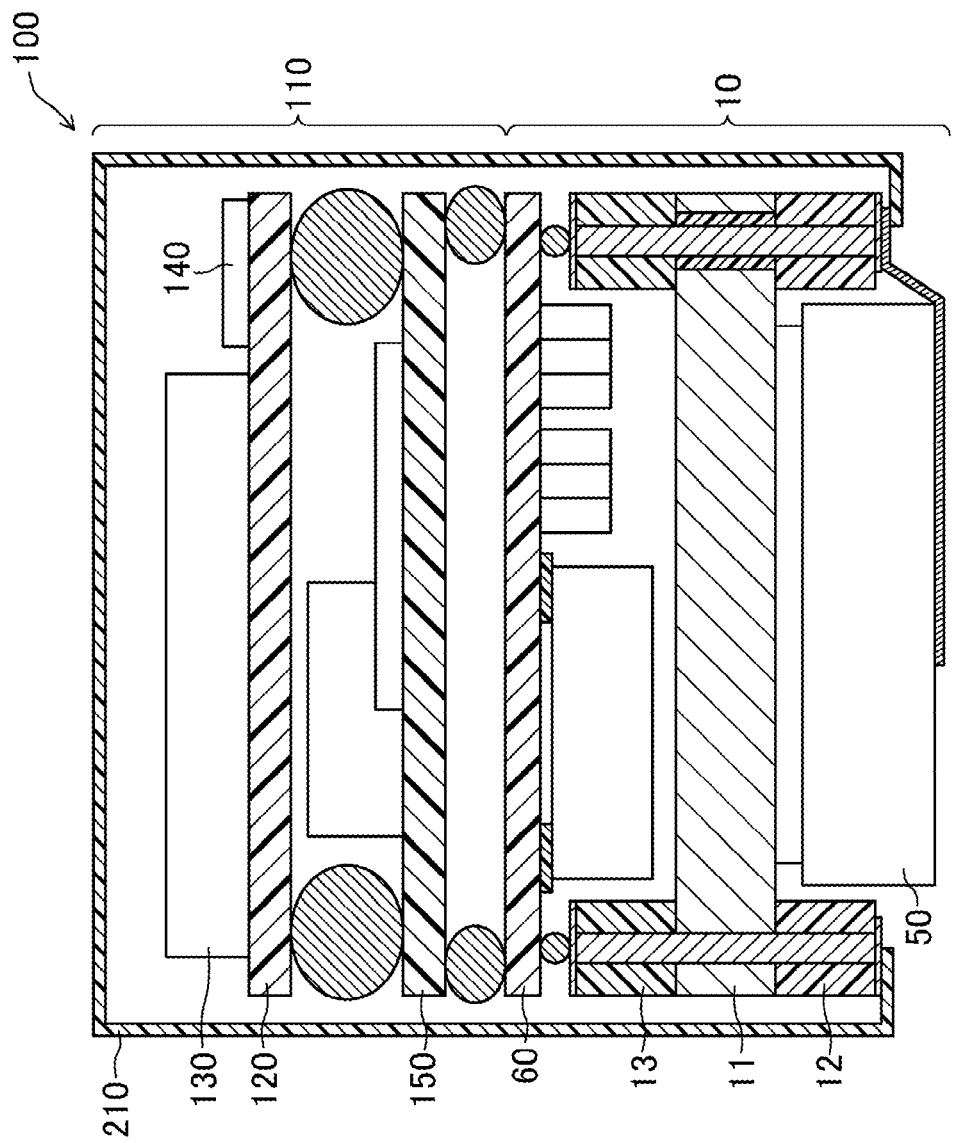
FIG. 9 is a sectional view illustrating another modified embodiment of the wireless sensor module.

Also, the wireless sensor module 100 of this exemplary embodiment may be molded with a resin 200 or may be covered with a case 210, as shown in FIGS. 8 and 9. In this case, the battery 50 is not covered with the mold resin or case so that the battery 50 can be attached and detached.

Also, instead of the configuration where the sensor 130 and the antenna 140 are mounted on the circuit board 120, the sensor 130 and the antenna 140 may be mounted on a surface of the circuit board 60, which is opposite to the surface on which the voltage conversion circuits 61, 62 are mounted.

Although the preferred exemplary embodiments of the present invention have been described, the technology is not limited to the exemplary embodiments and can be variously changed and modified.

Clauses

This disclosure further encompasses various exemplary embodiments, for example, described below.

1. A method of manufacturing a power supply module, the method comprising:

forming a first insulation layer and a second insulation layer respectively on a first surface and a second surface of a metal core substrate and embedding an insulation member in a thickness direction at a periphery of the metal core substrate;

forming a first through-electrode penetrating the second insulation layer in a first part at the periphery of the metal core substrate;

forming a second through-electrode penetrating the first insulation layer, the insulation member of the metal core substrate and the second insulation layer in a second part at the periphery of the metal core substrate;

removing the first insulation layer with being left at the periphery of the metal core substrate to expose the first surface of the metal core substrate;

mounting a battery on the first surface of the metal core substrate with one terminal being contacted to the first surface, and mounting a circuit board having a voltage conversion circuit at the second surface-side of the metal core substrate.

2. The method according to claim 1, wherein the forming the first through-electrode and the forming the second through-electrode are performed at the same time.

What is claimed is:

1. A package comprising:
a metal core substrate;
a first insulation layer formed along a periphery of a first surface of the metal core substrate, the first surface of the metal core substrate being exposed at an inner side of the first insulation layer;
a second insulation layer formed along at least a periphery of a second surface of the metal core substrate;
a first through-electrode penetrating the second insulation layer at a first part of the periphery of the metal core substrate; and
a second through-electrode penetrating the first insulation layer, the metal core substrate and the second insulation layer at a second part of the periphery of the metal core substrate, the second through-electrode being electrically insulated from the metal core substrate via an insulation member.

2. The package according to claim 1, wherein a first cavity defined by the first surface at which the metal core substrate is exposed and a side surface of the first insulation layer is formed at the inner side of the first insulation layer,
wherein a second cavity defined by the second surface at which the metal core substrate is exposed and a side surface of the second insulation layer is formed at an inner side of the second insulation layer.

3. The package according to claim 2, wherein the exposed first surface of the metal core substrate has a step portion.

4. The package according to claim 1, wherein the first through-electrode is configured to penetrate the first insulation layer, the metal core substrate and the second insulation layer.

5. A power supply module comprising:
a package according to claim 1;
a battery mounted on a metal core substrate; and
a circuit board mounted over the metal core substrate and having a voltage conversion circuit configured to convert a voltage of the battery into a predetermined voltage,
wherein the battery is mounted on the first surface of the metal core substrate at a state where one electrode terminal of the battery is contacted to the first surface,
wherein the circuit board having the voltage conversion circuit is mounted at the second surface-side of the metal core substrate,
wherein the one electrode terminal of the battery is connected to the first through-electrode via the metal core substrate,
wherein the other electrode terminal of the battery is connected to the second through-electrode exposed to a surface of the first insulation layer via a connection member, and
wherein potentials of both the electrode terminals of the battery are respectively supplied to the circuit board via the first through-electrode and the second through-electrode exposed to a surface of the second insulation layer.

6. The power supply module according to claim 5, wherein a first cavity defined by the first surface at which the metal core substrate is exposed and a side surface of the first insulation layer is formed at the inner side of the first insulation layer,
wherein a second cavity defined by the second surface at which the metal core substrate is exposed and a side surface of the second insulation layer is formed at an inner side of the second insulation layer, wherein the battery is accommodated in the first cavity, and wherein the voltage conversion circuit is accommodated in the second cavity.

7. The power supply module according to claim 5, wherein the battery is a coin type battery, and wherein at least a part of the first insulation layer has an arc-shaped side surface configured to contact an outer periphery of the coin type battery.

8. The power supply module according to claim 6, wherein the exposed first surface of the metal core substrate has a step portion, and the battery is accommodated in the first cavity and the step portion.

9. The power supply module according to claim 5, wherein the first through-electrode is configured to penetrate the first insulation layer, the metal core substrate and the second insulation layer.

10. A wireless sensor module comprising:

a power supply module according to claim 5; and an electronic device having a sensor, an antenna configured to transmit a detection signal detected at the sensor and a circuit board on which the sensor and the antenna are mounted, wherein the electronic device is stacked on the power supply module, and wherein an output voltage of the voltage conversion circuit of the power supply module is supplied as a driving voltage of the sensor.

* * * * *